United States Patent
Deisseroth

(10) Patent No.: US 10,383,932 B2
(45) Date of Patent: Aug. 20, 2019

(54) VACCINE DIRECTED TO INDUCTION OF IMMUNE RESPONSE TO PROTEIN AND GLYCOLIPID ANTIGENS OF BACTERIAL CELLS THROUGH INTERACTION OF CD4OL/CD40 RECEPTOR AXIS WITH COMPLEX OF GLYCOLIPID/CD1D RECEPTOR IN NKT CELLS AND IN DENDRITIC CELLS

(71) Applicant: Albert B. Deisseroth, Potomac, MD (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 488 days.

(21) Appl. No.: 15/138,511

(22) Filed: Apr. 26, 2016

(65) Prior Publication Data

US 2017/0239339 A1    Aug. 24, 2017

Related U.S. Application Data

(63) Continuation-in-part of application No. 14/163,206, filed on Jan. 24, 2014, now abandoned.

(60) Provisional application No. 61/776,875, filed on Mar. 12, 2013.

(51) Int. Cl.
*A61K 39/02* (2006.01)
*A61K 39/39* (2006.01)
*A61K 39/00* (2006.01)

(52) U.S. Cl.
CPC .......... *A61K 39/0208* (2013.01); *A61K 39/39* (2013.01); *A61K 2039/5256* (2013.01); *A61K 2039/572* (2013.01); *A61K 2039/6031* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 2005/0226888 A1 | 10/2005 | Deisseroth et al. | |
| 2008/0254045 A1* | 10/2008 | Donda | A61K 39/385 424/178.1 |

OTHER PUBLICATIONS

PCT International Search Report and Written Opinion issued for the corresponding international application No. PCT/US2017/029631, dated Aug. 14, 2017, 7 pages.
L. J. Carreno, et al.: "Synthetic glycolipid activators of natural killer T cells as immunotherapeutic agents." Clinical & Translational Immunology (2016) 5, e69; 9 pages.
Shin-ichiro Fujii, et al. "Activation of Natural Killer T Cells by Alpha-Galactosylceramide Rapidly Induces the Full Maturation of Dendritic Cells In Vivo and Thereby Acts as an Adjuvant for Combined CD4 and CD8 T Cell Immunity to a Coadministered Protein." J. Exp. Med. Jul. 21, 2003; vol. 198, No. 2; pp. 267-279.
Hidemitsu Kitamura, et al. "The Natural Killer T (NKT) Cell Ligand Alpha-Galactosylceramide Demonstrates Its Immunopotentiating Effect by Inducing Interleukin (IL)-12 Production by Dendritic Cells and IL-12 Receptor Expression on NKT Cells." J. Exp. Med. Apr. 5, 1999; vol. 189, No. 7; pp. 1121-1127.
Detlef Stober, et al. "NKT Cells Provide Help for Dendritic Cell-Dependent Priming of MHC Class I-Restricted CD8+ T Cells in Vivo." The Journal of Immunology, Mar. 3, 2003; vol. 170, No. 5; pp. 2540-2548.

* cited by examiner

*Primary Examiner* — Oluwatosin A Ogunbiyi
(74) *Attorney, Agent, or Firm* — Jacob Frank; Glenn Snyder

(57) ABSTRACT

A combination of components to promote an innate and adaptive immune response comprising of a TAA/ecdCD40L vaccine and a complex between the CD1d receptor and an alpha galactosyl ceramide like glycolipid (AGCLGL), to activate NKT cells and activate the CD40 receptor on the DCs and increase the level of the adaptive immune response induced by the TAA/ecdCD40L vaccine to the TAA. The result and advantage of using both the TAA/ecdCD40L vaccine and the α-galactosylceramide-CD1d complex (or a related bacterial or other antigen related to α-galactosylceramide) to stimulate the immune response through the CD40L/CD40 axis on dendritic cells, is that the magnitude of the stimulation is robust and increased significantly more than additive—i.e. synergistically due to the interaction, cross-talk and/or cross-stimulation of the glycolipid-CD1d pathway and TAA/ecdCD40L pathway. As a result, a potent immune response is induced against lipid target antigens as well as protein target antigens.

15 Claims, 5 Drawing Sheets
Specification includes a Sequence Listing.

Figure 1A: alpha galactosyl ceramide from marine sponges
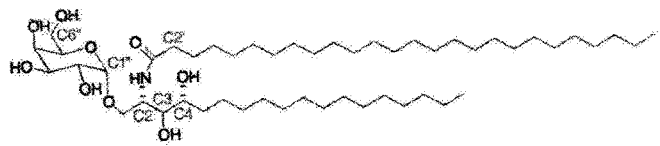
SEQ ID No. 1
Figure 1B: glycolipids from the cell wall of the Sphingomonas bacterial
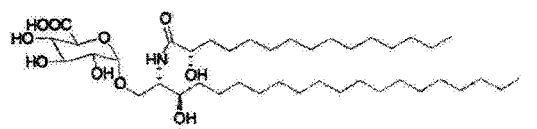
SEQ ID No. 2
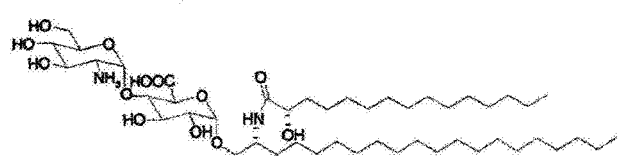
SEQ ID No. 3
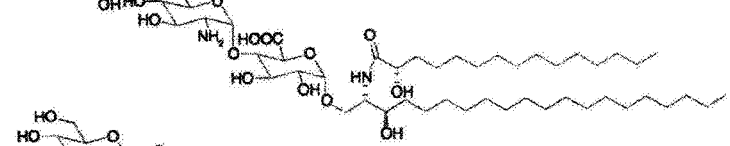
SEQ ID No. 4
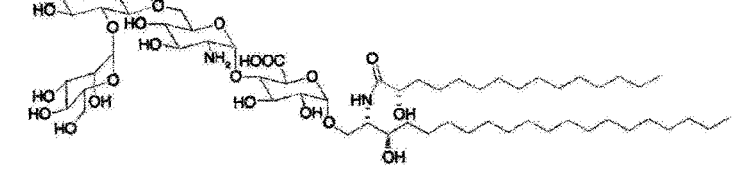
SEQ ID No. 5
Figure 1C: iGb3 (Mammalian isoglobotriihexosylceramide)
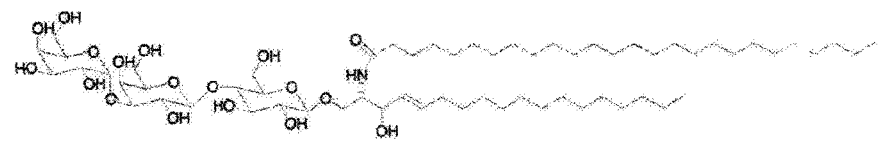
SEQ ID No. 6

FIG 1D

AA1-
AEVPQRLFPLRCLQISSFANSSWTRTDGLAWLGELQTHSWSNDSDTVRSLKPWSQGTFSDQQWETLQHIFRVYRSSFT
RDVKEFAKMRLSYPLSAGCEVHPGNASNNFFHVAFQGKDILSFQGTSWEPTQEAPLWVNLAIQVLNQDKWTRETVQ
WLLNGTCPQFVSGLLESGKSELKKQVKPKAWLSRGPSPGPGRLLLVCHVSGFYPKPVWVKWMRGEQEQQGTQPGDI
LPNADETWYRATLDVVAGEAAGLSCRVKHSSLEGQDIVLYWGGSYTS-AA282     SEQ ID No. 1

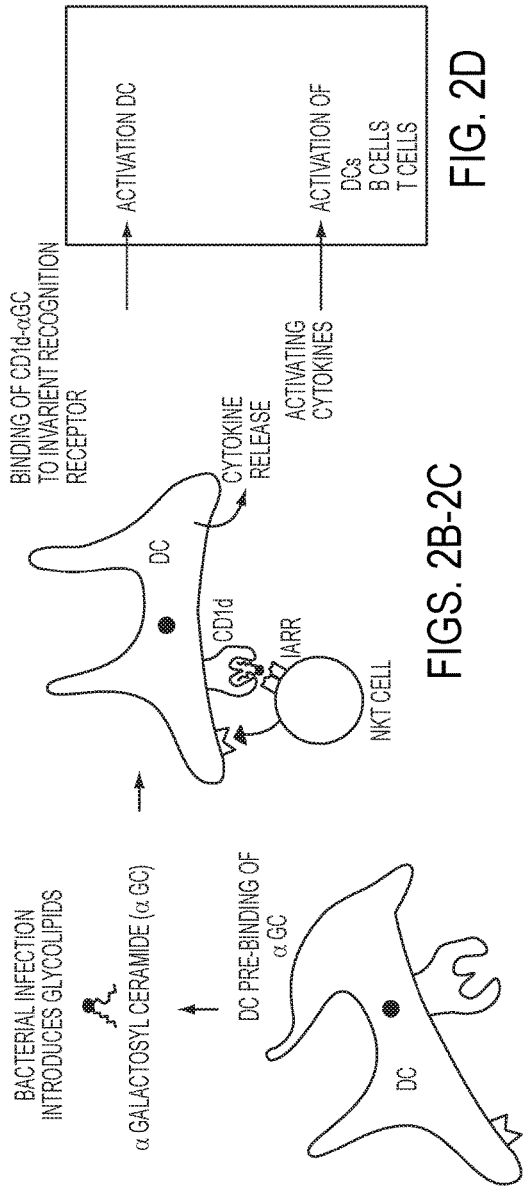
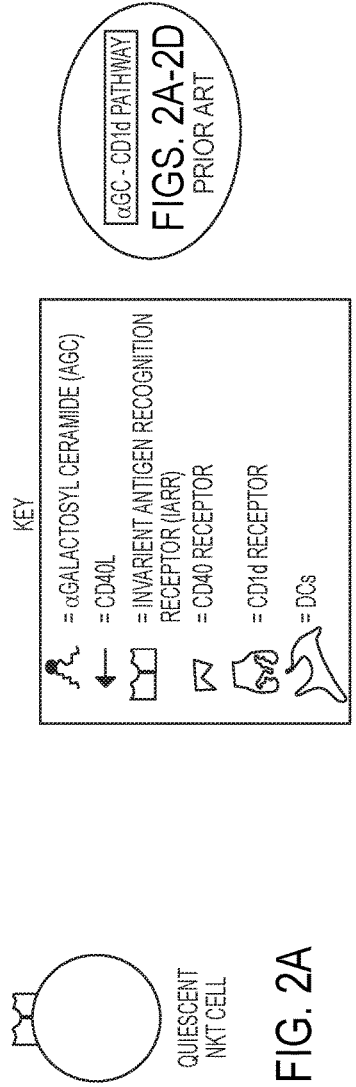
FIGS. 2B-2C
FIG. 2A
FIGS. 2A-2D
PRIOR ART

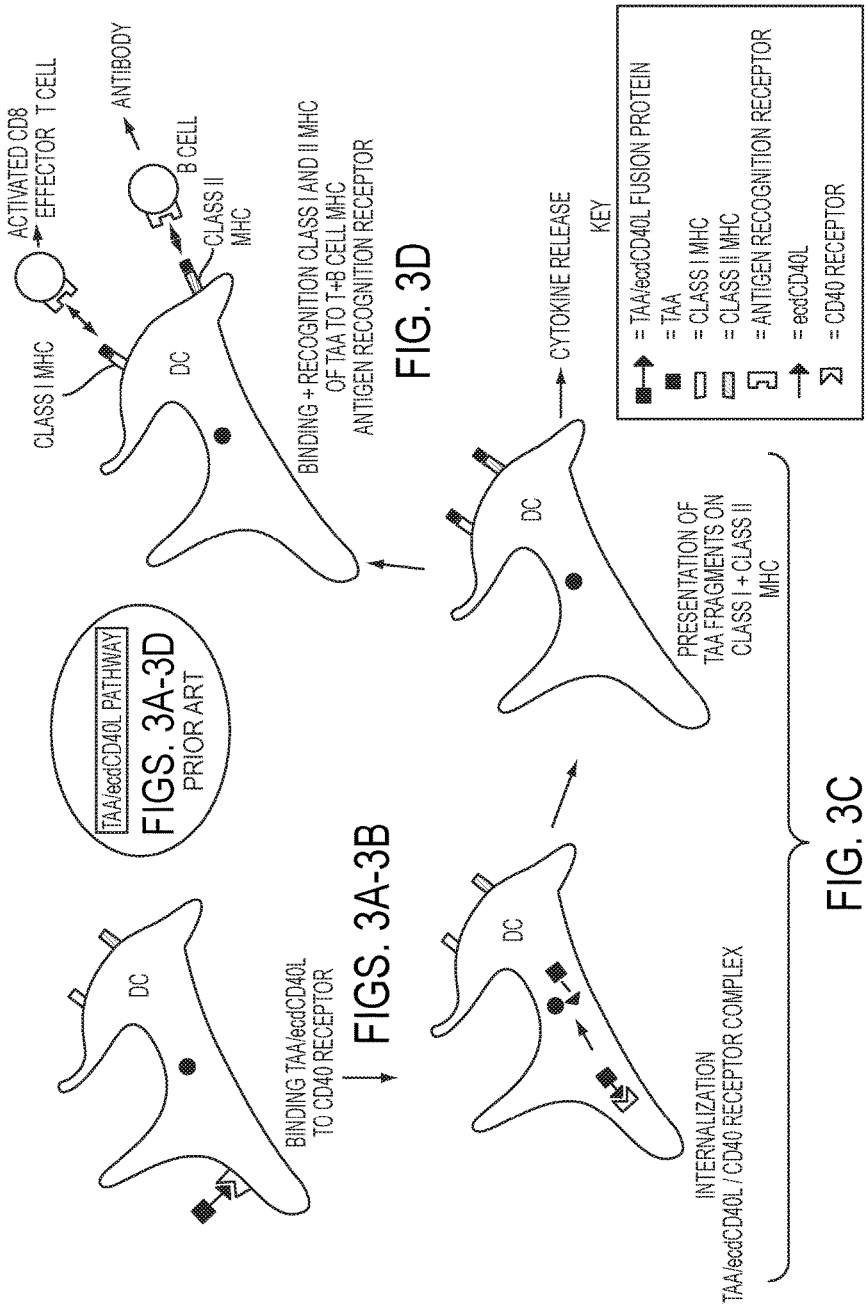

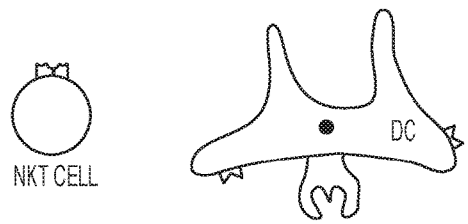
FIG. 4A
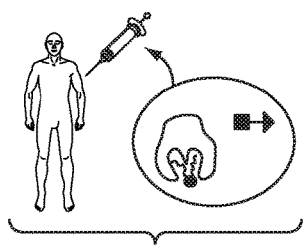
FIG. 4B
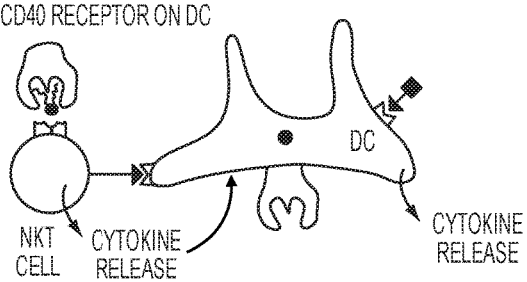
FIG. 4C
CROSSTALK BETWEEN AGC-CD1d AND TAA/ecdCD40L PATHWAYS PROMOTES MASSIVE CYTOKINE RELEASE TO POTENTLY STIMULATE DCs, B CELLS T CELLS, DCs PRESENT TO T CELLS + B CELLS
FIG. 4D

VACCINE DIRECTED TO INDUCTION OF IMMUNE RESPONSE TO PROTEIN AND GLYCOLIPID ANTIGENS OF BACTERIAL CELLS THROUGH INTERACTION OF CD40L/CD40 RECEPTOR AXIS WITH COMPLEX OF GLYCOLIPID/CD1D RECEPTOR IN NKT CELLS AND IN DENDRITIC CELLS

CROSS-REFERENCE TO RELATED APPLICATIONS

This application is a continuation-in-part of U.S. patent application Ser. No. 14/163,206 filed Jan. 24, 2014, which claims priority to U.S. Provisional Patent Application No. 61/776,875 filed on Mar. 12, 2013, the disclosures of which are both hereby incorporated herein by reference in their entireties.

FIELD OF THE INVENTION

The present invention relates to a vaccine composed of a complex of a glycolipid and theCD1d receptor combined with the TAA/ecdCD40L vaccine, for administration to an individual to simultaneously induce an innate immune response against protein antigens of bacterial cells and to amplify the adaptive immune response induced by the TAA/ecdCD40L against the target associated antigen (TAA).

BACKGROUND OF THE INVENTION

NKT Cells, the CD1d System and Glycolipids from Marine Sponges, Bacterial Cells, and Human Tissues (1).

NKT cells are defined by the expression of a semi-invariant, CD1d-restricted, alpha-beta T cell receptor (TCR). Most of these receptors are V$\alpha$14-J$\alpha$18/V$\beta$11 in structure. Human V$\alpha$24 NKT cells bind and react strongly to the CD1d receptor on dendritic cells, once this receptor is bound to certain glycolipids like alpha-galactosylceramide, the chemical structure of which is shown in FIG. 1A (originally isolated from the marine sponge: *Agelas mauritianus* which was first collected from the Okinawan Sea), and glycolipids isolated from the cell wall of *Sphingomonas* (the chemical structures of which are presented in FIG. 1B) which is a Gram-negative, LPS-negative member of the alpha-proteobacteria class (1). A mixture of the CD1d receptor mixed with either alpha-galactosylceramide, or the glycolipids shown in FIG. 1B from *Sphingomonas* (both of which are comprised of a sugar moiety linked to the ceramide lipid by an alpha glycolipid linkage (1) will induce activation of NKT cells through binding to the V$\alpha$14-J$\alpha$18/V$\beta$11 receptor on human V$\alpha$24 NKT cells (1). Experimental testing shows that the injection of such glycolipids into mouse tumor models induce tumor regressions and extends survival of tumor bearing mice (1). It is further noted that the glycospingolipids once bound to the CD1d receptor on dendritic cells are responsible for the strong stimulation of NKT cells and their role in clearing infections (1).

Mixtures of CD1d with the glycosphingolipid iGb3 (the chemical structure of which is presented in FIG. 1C, which is found in mouse and human tissues (1), induces activation of human NKT cells, also through binding of the V$\alpha$14-J$\alpha$18/V$\beta$11 receptor on human V$\alpha$24 NKT cells (1). The level on stimulation by iGb3 shown in FIG. 1C, in which a sugar moiety is linked to ceramide through a beta linkage, is much weaker that that seen with the glycolipids shown in FIGS. 1A and 1B, in which the sugar moiety is linked to the ceramide through an alpha linkage (1).

The CD1d receptor is a 37.713 kilodaltons (kDa) protein with 333 amino acids: 18 amino acids in the signal sequence, 282 amino acids in the extracellular domain, 23 amino acids in the transmembrane domain and 10 amino acids in the cytoplasmic domain (2). The aminoacid structure of the extracellular domain of the CD1d receptor (SEQ ID No. 1) is shown in FIG. 1D which is preferable although use of the entire CD1d protein (333 aminoacids) is acceptable. Both in vitro and in vivo experiments show that once any one of the glycolipids shown in FIGS. 1A-1C are mixed with the entire CD1d receptor or ecdCD1d receptor (FIG. 1D), the complex thus formed displays a high affinity to the V$\alpha$14-J$\alpha$18/V$\beta$11 receptor on human V$\alpha$24 NKT cells.

Non V$\alpha$24 NKT cells which are CD1d restricted may be involved in autoimmune diseases (1). The CD1d system of MHC like molecules on dendritic cells (DCs) are thought to present lipid antigens to T cells. The combination of alpha-galactosylceramide like glycolipids (AGCLGL) with the CD1d on DCs binds to the mouse TCR of the NKT cells with a dissociation constant (Kd) of 100 nM and with a Kd of 7 μM to the human TCR (1). This results in the activation of expression of ligands such as CD40L on the NKTs, and the release from the NKT cells of Th1 and Th2 cytokines and chemokines (see FIGS. 2A-2D). As a consequence of a bacterial infection these cytokines are released from the activated NKT cells along with the binding of the CD40L of the activated NKT cells to the CD40 receptor on the DCs and results in their activation (see FIGS. 2A-2D).

CD1d and MHC Presentation Molecules on DCs.

DCs become activated through binding of external ligands to plasma membrane receptors (e.g. the CD40 ligand/CD40 receptor) so as to increase expression of Class I and Class II MHC for the presentation of peptide fragments of target protein antigens to CD8 effector T cells (see FIG. 3) and to increase the level of expression of surface molecules like CD1d for presentation of lipid antigens like, for example, alpha-galactosylceramide (See FIGS. 2A-2D).

CD1d is expressed on DCs, cortical thymocytes, as well as B cells. CD1d is also found on hepatocytes in virally infected livers, as well as glial cells from inflamed tissues. CD1d is not found on any other cells except at very low levels.

Bacterial Glycolipids and NKT Cells.

Alpha-galactosyldiacylglycerols extracted from Gram-negative LPS negative organisms (such as *Borrelia burgdorferi* which causes Lyme disease) can directly stimulate NKT cells. Most of the evidence indicates that NKT cells and their hV$\alpha$24-J$\alpha$18 TCRs have the function of binding and recognizing $\alpha$-galactosylceramide (AGC) like glycolipid (AGCLGL) ligands from bacterial cells so as trigger an innate like immune response (1) as well as an adaptive immune response.

AGC was first isolated from the marine sponge *Agelas mauritanitus*. It was shown that when AGC binds to the CD1d receptor on DCs, it can bind to the invariant antigen recognition receptor (IARR) of NKT cells and activate them. AGCLCL antigens have been isolated from the following infectious agents which have been shown to bind CD1d resulting in the subsequent binding of the ACLGL-CD1d combination to the IARR of NKT: (i) monoglycosylcderamides from *Spongomonas* species, (ii) phosphatidylinositol mannosides from *Mycobacterium tuberculosis*, (iii) lipophosphoglycan from *Leishmania donovani*. These AGCLGL molecules presumably have similarities in structure to AGC. Applicant submits that all infectious antigens, foreign antigens and/or self-antigens, of any kind or character, that carry glycolipid molecules that are similar in structure, fall within the confines of Applicant's invention.

Mechanism of the Immune Response to Invading Bacterial Cells Positive for α-Galactosylceramide Like Glycolipid Ligands.

The invasion of a microbe positive for glycolipids similar to α-galactosylceramide leads to the binding of the α-galactosylceramide like antigens (AGCLGL) to the CD1d molecule expressed on resting DCs. The formation of the α-galactosylceramide-CD1d or AGCLGL-CD1d combination creates a structure which has a high binding affinity for the hVα24-Jα18 TCRs of NKT cells.

Binding of Glycolipids to CD1d on DCs Leads to Activation of the CD40L/CD40 Receptor Pathway.

The binding of the α-galactosylceramide-CD1d or AGCLGL-CD1d combination to the hVα24-Jα18 TCRs leads to activation of the NKT cells, with consequent increase of the level of the immunostimulatory molecule, CD40 ligand (CD40L), on the surface of the NKT cell (see FIGS. 2A-2D). In addition, the binding triggers the release from the NKT cells of large amounts of Th1 like cytokines (interferon-γ, IL-12, and interferon-α), Th2 like cytokines (IL-4), and increased expression of the B7.1 and B7.2 co-stimulatory molecules (1).

Interaction of NKT Cells and DCs.

The expression of the CD40L on the NKT cells then leads to binding of the CD40L on the NKT cell surface to the CD40 receptor on the DCs (see FIG. 2), the very same DCs which have the α-galactosylceramide bound to their own CD1d receptor. These α-galactosylceramide-CD1d combinations on the DC bind to the hVα24-Jα18 TCRs on the NKT cells. When the DC becomes activated by the CD40L of the activated NKT, then these DCs migrate to the draining lymph nodes where they present their α-galactosylceramide-CD1d or AGCLGL-CD1d combinations as well as their TAA to appropriate T and B cells to induce an adaptive immune response to the bacterial cell glycolipids and TAA.

Historical Summary of the Development of the TAA/ecdCD40L Vaccine Platform the Development of which the Applicant Participated as a Co-Inventor.

Previous Vaccines.

Vaccines have been described that include an adenoviral expression vector encoding a fusion protein that includes a target associated antigen (TAA) fused to the CD40 ligand (CD40L). See, e.g., U.S. Patent Application Publication US 2005-0226888 (application Ser. No. 11/009,533) titled "Methods for Generating Immunity to Antigen," filed Dec. 10, 2004.

The vaccine (see FIGS. 3A-3D) is based on the attachment of a fragment of a TAA fused to the extracellular domain (ecd) of the potent immunostimulatory signal CD40 ligand (CD40L). The TAA/ecdCD40L fusion protein vaccine can be administered either as a TAA/ecdCD40L protein, or as an expression vector encoding the TAA/ecdCD40L such as virus including the adenoviral vector: Ad-sig-TAA/ecdCD40L vector, or other viral vectors, or a plasmid DNA expression vector encoding the TAA/ecdCD40L protein (3-13). The vaccine can be also administered as an Ad-sig-TAA/ecdCD40L vector prime followed in 7 and 21 days with sc injections of the TAA/ecdCD40L protein vaccine. This vaccine platform was developed by the Applicant's laboratory (3-13) to overcome the following problems: weak immunogenicity of the target antigens, qualitative or quantitative defects of CD4 helper T cells, defective response in immunodeficient individuals including the older aged population due to diminished expression of CD40L in activated CD4 helper T cells, and/or low levels of presentation of target antigens on Class I or II MHC in dendritic cells (DCs). The CD40L is important for the expansion of antigen specific CD8 effector T cells and antigen specific B cells in response to vaccination.

Modes of Administration of TAA/ecdCD40L Vaccine.

There are four versions or modes of administration of this vaccine: 1. One in which the TAA/ecdCD40L transcription unit is embedded in a replication incompetent adenoviral vector (Ad-sig-TAA/ecdCD40L); 2. One in which the vector is used as an initial priming injection, followed by two sc injections of the TAA/ecdCD40L protein; 3. One in which the vaccine consists solely of the TAA/ecdCD40L protein; and 4. One in which the TAA/ecdCD40L is inserted into a plasmid DNA expression vector. The TAA is connected through a linker to the aminoterminal end of the ecd of the potent immunostimulatory signal CD40L.

Impact of Attachment of TAA to CD40L.

The attachment of fragments of the TAA to the CD40L accomplishes two things: 1. The binding of the TAA/ecdCD40L protein to the CD40 receptor on the DCs as well as on the B cells and T cells, activating these cells thereby promoting a potent immune response (3, 5, 7); 2. Once the TAA/ecdCD40L protein is engaged on the CD40 receptor of the DC, the entire TAA/ecdCD40L protein is internalized into the DC in a way that allows Class I as well as Class II MHC presentation of the TAA (3, 7).

Activation of DCs by TAA/ecdCD40L Vaccine.

The activated TAA loaded DCs then migrate to the regional lymph nodes (3, 7) where they can activate and induce expansion of the TAA specific CD8$^+$ effector T cells. The antigen specific CD8$^+$ effector T cells become increased in number in the lymph nodes (3, 7), and they then egress from the lymph nodes into the peripheral blood. The antigen specific CD8 effector T cells exit the intravascular compartment and enter into the extra-vascular sites of inflammation or infection (10, 11, and 13). In addition to showing that this vaccine increases the levels of the antigen specific CD8$^+$ effector T cells in the sites of inflammation or infection (12), the Applicant's laboratory has shown that the activation and expansion of the TAA specific B cells by the TAA/ecdCD40L protein increases the levels of the TAA specific antibodies (see FIGS. 3A-3D) including neutralizing antibodies against viral antigens in the serum (10, 11 and 13).

SUMMARY OF THE INVENTION

Aspects of the invention are based on the co-administration of the TAA/ecdCD40L vaccine or expression vector with a complex formed between either the CD1d receptor protein or the ecdCD1d receptor protein (FIG. 1D) and an AGCLGL (FIG. 1A) vaccine. The addition of a α-galactosylceramide-CD1d or AGCLGL-CD1d complex with the TAA/ecdCD40L vaccine or expression vector, further activates the CD40 receptor on DCs thereby promoting an increase in the magnitude of a cellular and humoral immune response to the TAA. The ecd of the CD1d receptor is used in the AGCLGL-CD1d complex without the transmembrane domain or cytoplasmic domain because all of the sequences necessary for the formation of the CD1d/AGCLGL complex are contained in the extracellular domain of the CD1d. The result and advantage of using both the TAA/ecdCD40L vaccine and the α-galactosylceramide-CD1d complex (or a related bacterial or other antigen related to α-galactosylceramide) to stimulate the immune response through the CD40L/CD40 axis on the DCs, is that the magnitude of the immune response induced against the TAA is increased significantly over what could be achieved by administration of either the fusion protein or vaccine alone. This is due to the cross-talk or cross-stimulation or interaction of the two glycolipid-CD1d and TAA/ecdCD40L DC pathways. As a result, a potent immune response is induced against the protein target antigens. As will be addressed in detail below preferred embodiments of the invention, the vaccine administrations may be done concurrently, or sequentially within prescribed periods of time.

The following comprises several aspects of Applicant's invention as to a new method and/or composition of matter, any one or more of which aspects are submitted to be an improvement over the prior art:

One aspect of the invention uses the vaccine combination of (i) a complex formed by the CD1d receptor bound to a AGCLGL, and (ii) a TAA/ecdCD40L fusion protein, to respectively induce both an innate and adaptive immune response in an individual.

Another aspect of the invention uses a combination of a complex formed between an AGCLGL and CD1d, and the vaccine comprised of a TAA/ecdCD40L fusion protein or an expression vector encoding the TAA/ecdCD40L fusion protein, to induce both an innate and adaptive immune response in an individual to the TAA and an innate immune response to the AGCLGL.

Yet another aspect of the invention takes advantage of the interaction of two classes of antigens and induce a increase in the adaptive immune response against the TAA and an increase in the innate immune response against both of these.

Further, other aspects of the invention gain the advantages of having a dual component composition (whether given at the same or different times), that can activate both the innate and adaptive immune response to the TAA, by driving the human response to a new and extraordinary level. As is well known, the cells of the innate immune system play a crucial part in the initiation and subsequent direction of adaptive immune responses, as well as participating in the removal of pathogens that have been targeted by an adaptive immune response.

As a consequence of the increased capability embodied in the makeup of Applicant's unique dual component composition, it is an additional object of the current invention to leverage the natural responses of the human innate and adaptive immune response in such a manner to not only promote their inter-relationship to activate one's overall immune response, but to engender crosstalk, interaction and/or stimulation that promotes a greater response to foreign pathogens in both time and potency.

The above and other aspects and other embodiments are described in detail below.

BRIEF DESCRIPTION OF THE DRAWINGS

FIGS. 1A-1D show the structures of glycolipids (FIG. 1A-FIG. 1C) in which a ceramide lipid molecule is linked to a sugar, which when bound to the CD1d receptor or ecdCD1d receptor (FIG. 1D) are able to induce activation of the NKT cells through binding of the Vα14-Jα18/Vβ11 receptor on human Vα24 NKT cells (1).

FIGS. 2A-2D show prior art pathway steps involved in the induction of an innate immune response which follows the appearance of a alpha galactosyl ceramide (AGC) like glycolipid as the result of a bacterial infection: alpha galactosyl ceramide like glycolipid (AGCLGL).

FIGS. 3A-3D shows prior art pathway steps involved in the induction of a TAA specific adaptive immune response by administration of the TAA/ecdCD40L vaccine.

FIGS. 4A-4D shows cross talk, stimulation and/or interaction between the AGC-CD1d complex and TAA/ecdCD40L pathways and the cells of the innate and adaptive immune responses as a result of administration of the AGC-CD1d complex vaccine and the TAA/ecdCD40L vaccine, where multiple forms of cross talk, stimulation and/or interaction occur.

DETAILED DESCRIPTION OF THE INVENTION

Definitions

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the terms "antigen" or "antigenic factors" refers broadly to any antigen to which a human, mammal, bird or other animal can generate an immune response. The terms "antigen" or "antigenic factors" as used herein refers broadly to a molecule that contains at least one antigenic determinant or epitope to which the immune response may be directed. The immune response may be cell-mediated, humoral or both. As is well known in the art, an antigen may be protein, carbohydrate, lipid, or nucleic acid or any combinations of these biomolecules. As is also well known in the art, an antigen may be native, recombinant or synthetic. For example, an antigen may include non-natural molecules such as polymers and the like. Antigens include both self-antigens and non-self antigens. As used herein, "antigenic determinant" (or epitope) refers to a single antigenic site on an antigen or antigenic factor; it is a minimal portion of a molecule that recognized by the immune system, specifically by antibodies, B cells or T cells. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein is an amount that results in an increase in the immune response as measured by an increase in T cell activity or antibody production.

The TAA/ecdCD40L fusion protein—a mixture recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, *Vaccine* 5:223 (1987)), monophosphoryl lipid A (Johnson et al., *Rev. Infect. Dis.* 9:S512 (198)), and the like.

The term "vector" as used in this application contains a transcription unit (also known as an "expression vector"). It encompasses both viral and non-viral expression vectors that when administered in vivo can enter target cells and express an encoded protein. Viral vectors have evolved means to overcome cellular barriers and immune defense mechanisms. Viral vectors suitable for in vivo delivery and expression of an exogenous protein are well known in the art and include adenoviral vectors, adeno-associated viral vectors, retroviral vectors, vaccinia vectors, pox vectors, herpes simplex viral vectors, etc. Viral vectors are preferably made replication defective in normal cells. For example, see U.S. Pat. Nos. 6,669,942; 6,566,128; 6,794,188; 6,110,744 and 6,133,029.

On the other hand, non-viral gene carriers consistently exhibit significantly reduced transfection efficiency as they are hindered by numerous extra- and intracellular obstacles. Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture is useful as a vehicle for non-viral expression vectors. See U.S. Pat. No. 6,147,055. Polycation-DNA complexes also may be used as a nonviral gene delivery vehicle. See Thomas et al., *Appl Microbiol Biotechnol* (2003) 62(1):27-34. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered subcutaneously.

The term "transcription unit" as used herein in connection with an expression vector means a stretch of DNA, that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element(s). One useful promoter/enhancer is the cytomegalovirus (CMV) immediate-early promoter/enhancer. See U.S. Pat. Nos. 5,849,522 and 6,218,140.

The term "secretory signal sequence" (also known as "signal sequence," "signal peptide," leader sequence, "or leader peptide") as used herein refers to a short peptide sequence, generally hydrophobic in charter, including about 20 to 30 amino acids that is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments, the endogenous tumor antigen signal sequence also may be used to direct secretion.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "antibody" as used herein (includes but is not limited to neutralizing antibodies) refers, for example, to antibodies that block, neutralize or otherwise act against the infectious foreign antigen.

The term "linker" as used or employed in this application with respect to the transcription unit of the expression vector refers to one or more amino acid residues between the carboxyl terminal end of the antigen and the amino terminal end of CD40 ligand. The composition and length of the linker may be determined in accordance with methods well known in the art and may be tested for efficacy. (See, e.g. Arai et al. *Protein Engineering*, Vol. 4, No. 8, 529-532, August 2001). In certain embodiments of the present invention, the linker is from about 3 to about 15 amino acids long, more preferably from about 5 to about 10 amino acids long. However, longer or shorter linkers may be used or the linker may not be used at all. Longer linkers may be up to about 50 amino acids, or up to about 100 amino acids. One example of a linker well known in the art is a 15 amino acid linker consisting of three repeats of four glycines and a serine (i.e., [Gly$_4$Ser$_3$)].

The term "TAA" recited herein refers to a target associated antigen, which may, for example, be a viral antigen, a bacterial antigen, a tumor antigen, etc.

The term "crosstalk" or "cross-stimulation" or "stimulation" or "interaction", as a result of the administration of an AGC like glycolipid (AGCLGL) complexed with an CD1d receptor along with the TAA/ecdCD40L vaccine (see FIG. 4) as used herein means that the CD40L on the AGCLGL-CD1d receptor activated NKT cells stimulates the DCs which are presenting TAA as well as glycolipids. In addition, it means that the release of cytokines from the NKT cells activated by the administration of an AGC like glycolipid (AGCLGL) complexed with an CD1d receptor along with the TAA/ecdCD40L vaccine stimulates both pathways by inducing the release of cytokines from both the NKT cells as well as the DCs that further promote and further amplify the immune response induced by the TAA/ecdCD40L vaccine. Biological crosstalk generally refers to instances in which one or more components of one signal transduction pathway affect another. This can be achieved through a number of ways with the most common form being crosstalk between proteins of signaling cascades. In these signal transduction pathways, there are often shared components that can interact with either pathway.

The terms "pathway" or "biological pathway" as used herein is a series of actions among molecules in a cell that leads to a certain product or a change in a cell. Such a pathway can trigger the assembly of new molecules, such as a fat or protein. Cells are constantly receiving cues from both inside and outside the body, which are prompted by such things as injury, infection, stress or even food. To react and adjust to these cues, cells send and receive signals through biological pathways. The molecules that make up biological pathways interact with signals, as well as with each other, to carry out their designated tasks.

AGC was first isolated from the marine sponge *Agelas mauritanitus*. It was shown that when AGC binds to the CD1d receptor, it can bind to the invariant antigen receptor (IARR) of NKT cells and activate them. The term "AGC" means α-galactosylceramide. However, there are equivalent molecules that have similarities in structure to AGC (i.e. AGCLGL). For example, antigens have been isolated from the following infectious agents and been shown to bind CD1d and then to bind the IARR of the NKT: a. monoglycosylcderamides from *Spongomonas* species, b. phosphatidylinositol mannosides from *Mycobacterium tuberculosis*, and c. lipophosphoglycan from *Leishmania donovani*.

List of Abbreviations

Some of the abbreviations used in the instant application:
Ad—Adenoviral
AGC—α-galactosylceramide
CD40L—CD40 ligand
CD1d—non-classical MHC class 1b molecule
CMV—Cytomegalovirus
DCs—dendritic cells
ecd—extracellular domain
IARR—invariant antigen recognition receptor
SC—subcutaneous or subcutaneously
Sig—signal sequence
TAA—Target Associated Antigen Applicant's inventive composition of a complex component and a vaccine component, among other features, creates an anti-bacterial composition which is (i) very potent and induces a robust immune response against both peptide and glycolipid bacterial antigens, (ii) reduces the virulence of the bacterial cell, and (iii) prevents progression of an existing bacterial cell infection.

A chimeric α-galactosylceramide like glycolipid (AGCLGL) shown in FIG. 1A is complexed ex vivo with the CD1d receptor or ecdCD1d receptor (FIG. 1D) produced as recombinant biological. This complex is then preferably administered subcutaneously (sc) or intratumorally along with a vaccine comprised of a target associated protein antigen (TAA) fused through a linker to the ecd of the CD40L. An example of a method of forming the complex between alpha galactosylceramide (FIG. 1A) and the CD1d receptor is as outlined by the following steps, adapted by the method of Sriram et al (14). Lyophilized powder of alpha galactosyl ceramide is dissolved in 0.05% Tween-20 and then various dilutions are made in phosphate buffered saline (pH=7.4) with sonication. Dimeric CD1d-IgG which was purchased from Pharmingen, was mixed in different ratios of the solution of alpha galactosylceramide (as shown in FIG. 1A) and incubated overnight at 37 degrees C. These complexes were either added to NKT target cells in vitro or were injected subcutaneously into areas of test mice that had been injected 10 days earlier with adenoviral vectors or plasmid expression vectors which encode the TAA/ecdCD40L vaccine.

The TAA/ecdCD40L expression vector is made by the following steps. Synthesize a 30-40 AA long target associated antigen connected at its carboxylterminal end to the aminoterminal end of a 10 amino acid linker which is in turn attached at its carboxylterminal end to the aminoterminal end of the ecdCD40L. This TAA/ecdCD40L transcription unit is inserted into a plasmid expression vector downstream of a strong transcriptional promoter (e.g. CMV) by standard techniques.

The interaction of the AGCLGL-CD1d receptor activated NKT cells with the dendritic cells (DCs) through the CD40L/CD40 receptor axis that is activated by this combination, will not only trigger a massive cytokine release and activation of multiple components of the innate immune response but also induce an increased and robust cellular and humoral and cellular adaptive immune response against glycolipid antigens, protein antigens, and virulence proteins of the bacterial cell.

Pathways—the Biological Pathways of AGC-CD1d and TAA/ecdCD40L—the AGC-CD1d or AGCLGL-CD1d Pathway—

In FIG. 2 there is depicted the steps in the induction of an innate immune response which follows the appearance of a glycolipid: alpha galactosyl ceramide (AGC) or alpha galactosyl ceramide like glycolipid (AGCLGL) as a result of a bacterial infection:

Step 2a: Appearance of the alpha galactosyl ceramide (AGC) or AGCLGL as the result of a bacterial infection at the initial site of infection which is usually near the surfaces of the body in tissues which are rich in dendritic cells (DCs) as shown in FIG. 2A.

Step 2b: Binding of the AGC or AGCLGL complexed to CD1d on DCs to the invariant antigen recognition receptor (IARR) of the NKT cell which activates the NKT cell (as shown in FIG. 2B-C).

Step 2c: Activation of NKT cells results in a. release of cytokines stimulatory to the induction of an immune response (e.g. IL-12 or gamma interferon or many others) from the NKT cell, and b. appearance of the CD40 ligand (CD40L) on the surface of the NKT cell, as shown in FIG. 2 B-C.

Step 2d: Binding of the CD40L on the NKT cell to the CD40 receptor on the DCs which results in activation of the DCs as shown in FIG. 2B-C.

Step 2d: Activation of NKT cells results in further release of cytokines stimulatory of an adaptive and innate immune response (e.g. IL-12), as shown in FIG. 2B-C.

Step 2e: The cytokines released bind to and activate the following cells: monocytes, DCs, B cell lymphocytes, CD4 helper T cells, and CD8+ effector T cells resulting in the appearance of Class I and Class II MHC on the surface of the DCs, the appearance of intercellular cytoadhesion molecules like CD88 and CD86 on the surface of the DC, and the activation of the T cell and B cell lymphocytes (see FIG. 2D).

The TAA/ecdCD40L Pathway—

In FIG. 3 there is depicted the steps involved in the induction of a TAA specific adaptive immune response by administration of the TAA/ecdCD40L vaccine.

Step 3a: Administration of the TAA/ecdCD40L vaccine either as the TAA/ecdCD40L protein, or as an expression vector which carries a transcription unit which encodes the TAA/ecdCD40L protein which then induces the in vivo release of the TAA/ecdCD40L as shown in FIG. 3A-B.

Step 3b: The TAA/ecdCD40L fusion protein is taken up into the DC by CD40 receptor mediated endocytosis in a way that promotes presentation of fragments of TAA on both Class I and Class II MHC (see FIG. 3C).

Step 3c: Binding of the TAA/ecdCD40L fusion protein (at the C-ter which contains the ecdCD40L) to the CD40 receptor on DCs, CD8+ effector T cells, B cells, and CD4 helper T cells which activates the DCs (induces expression of IL2, IL2 receptor, CD88 and CD86 on DCs), increases expression of CD40L on the CD4 helper T cells, and facilitates expansion of TAA specific CD8+ effector T cells and B cells, if they are responding to TAA which are independently presented on Class I or Class II MHC (respectively) on DCs, as shown in FIG. 3D.

Step 3d: Presentation of TAA fragments on Class I and Class II MHC on DCs as shown in FIG. 3D.

Step 3e: Activation and induction of expansion of the TAA specific B cells and TAA specific CD8+ effector T cells, as shown in FIG. 3D.

Step 3f: Increase in the levels of TAA specific antibodies in the intravascular space and TAA specific CD8+ effector T cells at sites of infection or inflammation (cancer), as shown in FIG. 3D.

Cross Talk/Stimulation/Interaction Between the AGC-CD1d or AGCLGL-CD1d and TAA/ecdCD40L Pathways In FIG. 4 there is depicted as a result of simultaneous administration of the AGC-CD1d or AGCLGL-CD1d complex and the TAA/ecdCD40L vaccine, the induction of the following forms of cross talk between cells of the innate and adaptive immune response which amplifies the magnitude of the immune response otherwise induced by administration of the TAA/ecdCD40L vaccine alone.

4a. In FIG. 4A, is shown the state of the NKT cell and the DC prior to the administration of a vaccine comprised of an AGC like glycolipid complexed with an CD1d receptor along with the TAA/ecdCD40L vaccine. Note that no CD40L is present on the surface of NKT cells, and that there is no cytokine release from either the DC or the NKT cell.

4b. In FIG. 4B, is shown the co-administration of a complex of an AGC like glycolipid with an CD1d receptor (in the circle) together with the TAA/ecdCD40L fusion protein vaccine to a human subject's arm. Although in FIG. 4B, the complex of a AGCLGL with a CD1d receptor and the TAA/ecdCD40L fusion protein, are depicted administered together, as noted in FIG. 4C (in 4c below) the complex of a AGCLGL with a CD1d receptor and the TAA/ecdCD40L fusion protein vaccine, are shown injected separately.

4c: In FIG. 4C is shown that the administration of an AGC like glycolipid (see, for example, in FIG. 1A) complexed with an CD1d receptor or ecdCD1d receptor (see SEQ ID No. 1 in FIG. 1D), along with the TAA/ecdCD40L fusion protein vaccine which results in the binding of the glycolipid CD1d receptor complex to the IARR of the NKT cells with the resultant activation of the NKT cells which results in the appearance of CD40L on the surface of the NKT cell and the release of cytokines from NKT cells. This in turn results in the binding of the CD40L on the NKT cell to the CD40 receptor on the DC as well as the NKT cell cytokine release stimulation of the DCs which induces a release of cytokines from them as well as the appearance of a family of cytoadesion molecules of the DCs which further promote the development of an adaptive immune response as a result of the administration of the TAA/ecdCD40L. Finally, as shown in FIG. 4D, the result of the induction of the cytokine release from both NKT cells and DCs, as well as the engagement of the CD40 receptor on DCs by the CD40L on the activated NKT cells as well as the engagement of the CD40 receptor on DCs, B cells and T cells by the CD40L in the TAA/ecdCD40L vaccine, is that the activated and antigen loaded DCs present the TAA to B cells and T cells which have already been primed to respond by the prior cytokine release and CD40L stimulation.

This results in enhancement of the response of TAA specific B cells and CD8+ effector T cells to TAA presented by DCs by the cytokines released from the activation of the NKT cells (see FIG. 4D).

The administration of both the AGCLGL-CD1d receptor complex and the TAA/ecdCD40L vaccine, lead to amplification of the NKT response against the bacterial cells, and amplification of the induction of a robust innate as well as adaptive humoral and cellular immune response against the infectious agent.

Delivery of the Glycolipid-CD1d and TAA/ecdCD40L Vaccines Induces Cross-Talk Between NKT Cells and DCs.

The AGCLGL-CD1d receptor complex is delivered sc along with the TAA/ecdCD40L vaccine (see FIG. 4B). The glycolipid-CD1d complex will induce an innate immune response to a bacterial glycolipid antigen (see FIG. 2) and amplify the magnitude of the TAA/ecdCD40L vaccine induced adaptive immune response to a peptide antigen (see FIG. 3C). As a consequence of cross-talk or interaction between these two parallel pathways which intersect at the CD40 receptor on the DC, there will be additional stimulation (i.e. synergistic and robust) of the immune response to both the bacterial glycolipids and TAA peptides. Crosstalk or interaction means that the CD40L on the NKT cells as well as the TAA/ecdCD40L vaccine stimulates the DCs which are presenting TAA as well as glycolipids (see FIG. 4C). In addition, the release of cytokines from the NKT cells activated by the DCs carrying glycolipids on their CD1d receptor as well as the release of cytokines from the DCs bound to the TAA/ecdCD40L vaccine stimulates both pathways (see FIG. 4D).

The t immune response to glycolipid and or peptide may be induced independent of the order of the administration. If one administers the glycolipid-CD1d receptor complex first and then after a time interval administer the TAA/ecdCD40L, there will be an amplification of the immune response.

If one administers the TAA/ecdCD40L first and then after a time interval the glycolipid-CD1d receptor complex, then there will be an amplification of the immune response.

If one administers both at the same time, then the magnitude of the immune response will be higher than if either is administered alone.

This is due to the stimulation of the DCs by engagement of the CD40 receptor by CD40L from two pathways instead of from just one. In addition, cytokine release is from the activated NKT cells (in the AGCLGL-CD1d pathway) as well as from the DCs which are activated in the TAA/ecdCD40L pathway.

Details of Cross Talk/Stimulation/Interaction Between NKT Cells and DCs.

The cross-talk comprises of the release of cytokines and points of stimulation as follows:
a) The stimulation of the NKT cells by binding of the AGCLGL-CD1d receptor preformed complex.
b) The release from the NKT cells of a high level of cytokines and chemokines which stimulate both the AGCLGL-CD1d pathway as well as the TAA/ecdCD40L pathway. This NKT dependent cytokine release is added to that already induced from the DCs in the TAA/ecdCD40L pathway. These cytokines stimulate DCs, B cells, T cells, and monocytes.
c) The induction of expression of CD40L on the NKT cells as a result of the binding of the AGCLGL-CD1d receptor complex to the invariant antigen recognition receptor on the NKT cells.
d) The activation of the DCs by binding of the CD40L of the NKT cells to the CD40 receptor on DCs as well as the activation of the DCs by binding of the CD40 receptor by the TAA/ecdCD40L vaccine thus creating a robust stimulation of the DCs by CD40L from two different pathways.
e) All of these events leading to CD40L activation of the DCs and stimulation of all the cells of the immune response released from activated NKT cells as well as DCs by the dual component complex-vaccine strategy.

The combination of the AGCLGL-CD1d receptor delivered as pre-formed complex, and the TAA/ecdCD40L vaccine fusion molecule delivered as a plasmid DNA or viral expression vector will act to stimulate the CD40 receptor axis for the presentation of antigens of bacterial cells. The TAA/ecdCD40L can be administered as a chimeric protein, or as expression vectors which encode the TAA/ecdCD40L. Because both of these molecules will trigger directly or indirectly the activation of the CD40 axis, the magnitude of the immune response is increased as a consequence of the co-administration.

In the above discussion, the TAA referred to are from bacterial cells. But the same strategy would apply to foreign antigens on other infectious agents such as viruses, as well as tumor cells.

The steps involved in each of the AGCLGL-CD1d receptor complex and TAA/ecdCD40L pathways are summarized in FIGS. 2-3. In FIG. 4 is summarized the consequences of the administration of the AGCLGL-CD1d complex along with the TAA/ecdCD40L vaccine on stimulating cross talk between NKT cells and DCs resulting in an increase in the magnitude of the immune response induced by the TAA/ecdCD40L vaccine.

Advantages of the NKT Glycolipid-CD1d Complex-TAA/CD40L-Vaccine Strategy.

The co-administration of the complex and vaccine components will not only trigger a massive cytokine release and activation of multiple components of the innate immune response against the TAA as well as against the glycolipid of the bacterial cell but also induce a cellular and humoral adaptive immune response against the surface proteins and protein virulence factors of the bacterial cell.

Up to the present time, no vaccine strategy such as Applicant's has been developed which could induce simultaneously an immune response against bacterial lipids as well as protein antigens. In addition, this is the first strategy which utilizes dual stimulation of the CD40L/CD40 receptor pathway. Thus, not only will there be induction of an immune response to the peptide as well as the lipid antigens of the bacterial cell, but the use of the stimulators of the NKT cell and the dendritic cell will produce amplification of the magnitude of the activation of the immune response through the CD40L/CD40 receptor pathway.

Embodiments are set forth within the claims that follow.

REFERENCES

1. Bendelac A, Savage P G, and Teyto L. The biology of NKT Cells. Annual Review of Immunology 25: 297-336, (2007).
2. Zhang P, Li D, Stewart-Jones G, Shao X, Zhang Y X, Chen Q G, Li Y J, He Y W, Xy X B and Xhang H T. Immunology 128: 500-510, (2009).
3. Zhang, L, Tang, Y, Akbulut H, Zelterman D, Linton P-J, and Deisseroth, A. An adenoviral vector cancer vaccine that delivers a tumor-associated antigen/CD40-ligand fusion protein to dendritic cells. PNAS, 100: 15101-15106, (2003).
4. Akbulut, H, Tang, Y, Maynard J, Zhang L, Pizzorno G, and Deisseroth, A. Vector targeting makes 5-fluorouracil chemotherapy less toxic and more effective in animal models of epithelial neoplasms. Clin Cancer Res 10: 7738-7746, (2004).
5. Tang, Y, Zhang, L, Yuan, J, Akbulut H, Maynard J, Linton P-J, and Deisseroth, A. Multistep process through which adenoviral vector vaccine overcomes anergy to tumor-associated antigens. Blood, 104: 2704-2713, (2004).
6. Akbulut H, Tang Y C, Akbulut K G, Maynard J, Zhang L, Deisseroth A. Antitumor immune response induced by i.t. injection of vector activated dendritic cells and chemotherapy suppresses metastatic breast cancer. Mol Cancer Ther 5:1975-1985, (2006).
7. Tang Y C, Maynard J, Akbulut H, Fang X M, Zhang W W, Xia X Q, Koziol J, Linton P-J, and Deisseroth A. Vaccine which overcomes defects acquired during aging and cancer. Journal of Immunology 177:5697-5707, (2006).
8. Tang Y, Akbulut H, Maynard J, Zhang L, Petersen L, and Deisseroth A. Vaccine strategies for cancer and infectious diseases in the elderly. Gene Therapy, Eds. Takenori Ochiai, Hideaki Shimada, and Masatoshi Tagawa, Published by Japanese Ministry of Education and Science, pp. 78-85, (2007).
9. Akbulut H, Akbulut K G, Tang Y C, Maynard J and Deisseroth A. Chemotherapy targeted to cancer tissue potentiates antigen specific immune response induced by vaccine for In vivo antigen loading and activation of dendritic cells. Molecular Therapy, 10:1753-1760, (2008).
10. Tang, Y C, Linton, P J, Thoman M, and Deisseroth A. Symposium in Writing: Vaccine for infections and cancer. Cancer Immunology and Immunotherapy, 58: 1949-1957, (2009).
11. Han T H, Tang, Y C, Park Y H, Petersen L, Maynard J, Li P C, and Deisseroth A. Ad-sig-BcrAb1/ecdCD40L vector prime-BcrAb1/ecdCD40L protein boost vaccine for P210Bcr-Abl protein. Bone Marrow Transplantation, (2009).
12. Akbulut H, Tang Y, Akbulut K G, Maynard J, and Deisseroth A. Addition of adenoviral vector targeting of chemotherapy to the MUC-1/ecdCD40L VPPP vector prime protein boost vaccine prolongs survival of mice carrying growing subcutaneous deposits of Lewis lung cancer cells. Gene Therapy, 17: 1333-1340, (2010).

13. Deisseroth A, Tang Y, Zhang L, Akbulut H, and Habib N. TAA/ecdCD40L adenoviral prime-protein boost vaccine for cancer and infectious diseases. Cancer Gene Therapy 20: 65-69, (2013).

14. Sriram V, Du W J, Gervay-Hague J, and Brutkiewicz R R. Cell wall glycosphingolipids of *Sphingomonas paucimobilis* are CD1d-specific ligands for NKT cells. European Journal of Immunology 35: 1692-1701, (2005).

The invention claimed is:

1. A method for activating an individual's innate and adaptive immune response by the administration to the individual of a two component composition, said composition comprising:
   (i) a first component comprising an effective amount of a complex comprising an alpha galactosyl ceramide like glycolipid (AGCLGL) bound to the CD1d protein (AGCLGL-ecdCD1d) to promote activation of NKT cells and activation of an individual's dendritic cells, and T cell lymphocytes; and
   (ii) a second component comprising an effective amount of the fusion protein vaccine comprising a target associated antigen fused to the ecd of the CD40L (TAA/CD40L) configured to promote activation of dendritic cells and activation and expansion of TAA specific cytotoxic CD8+ effector T cells and TAA B cells inducing the release of TAA specific antibodies;
   (iii) wherein said administration of said composition is adapted to promote interaction through a CD40L/CD40 axis on dendritic cells.

2. The method according to claim 1 wherein said composition is administered subcutaneously.

3. The method of claim 1 wherein said composition is administered intratumorally.

4. The method of claim 1 wherein said fusion protein is encoded by an adenoviral expression vector encoding the TAA/ecdCD40L.

5. The method of claim 1 wherein said fusion protein is encoded by a plasmid DNA expression vector encoding the TAA/ecdCD40L protein.

6. A composition comprising two components for administration to an individual, comprising: (i) a first component complex of an AGCLGL with an ecdCD1d protein receptor; and, (ii) a second component TAA/ecdCD40L fusion protein,
   wherein said composition, induces innate and adaptive humoral and cellular immune responses against the TAA, and amplifies the immune response against the TAA by way of the interaction through a CD40L/CD40 axis on dendritic cells for increasing the immune response against the TAA over an immune response increase which the second component when used alone could achieve.

7. A composition according to claim 6, wherein said complex comprises an effective amount of said AGCLGL-ecdCD1d receptor for promoting activation of NKT cells, and said fusion protein comprises an effective amount of TAA/ecdCD40L for promoting activation of cytotoxic CD8+ effector T cells.

8. A composition according to claim 7 wherein said TAA in said fusion protein is connected to the aminoterminal of the ecd of said CD40L.

9. An anti-bacterial composition for generating an individual's innate and adaptive immune response, said composition comprising:
   (i) an AGCLGL bacterial antigenic fragment complexed ex vivo with an ecdCD1d receptor, produced as recombinant biological;
   (ii) a target associated protein antigen (TAA) fused through a linker to the ecd of the amino-terminal end of a CD40L protein defining a fusion protein, wherein the TAA is a bacterial antigen; and,
      wherein said complex and TAA/ecdCD40L collectively amplify the TAA immune response over an immune response increase which the TAA/ecdCD40L used alone could achieve, through the CD40L/CD40 axis on dendritic cells, and induces antigen specific innate and antigen specific adaptive humoral and cellular immune responses.

10. A composition according to claim 9 wherein the combination of said recombinant biological and said fusion protein promotes cross-stimulation in their respective biological pathways.

11. The composition of claim 9 wherein said fusion protein is encoded by an adenoviral expression vector encoding the TAA/ecdCD40L.

12. The composition of claim 9 wherein said fusion protein is encoded by a plasmid DNA expression vector encoding the TAA/ecdCD40L protein.

13. A composition which promotes an individual's innate and adaptive immune response against a foreign antigen, through the CD40/CD40L axis on dendritic cells, said composition comprising:
   (i) a complex of an AGCLGL with a CD1d receptor;
   (ii) a TAA/ecdCD40L fusion protein, wherein the TAA is a foreign antigen; and, wherein said composition, promotes an antigen specific innate immune response and an antigen specific adaptive immune response, and promotes crosstalk between biological pathways generated by the combination of AGCLGL-CD1d receptor and TAA/ecdCD40L fusion protein which crosstalk amplifies the individual's immune response against the TAA foreign antigen over that immune response increase which the TAA/ecdCD40L fusion protein used alone could achieve.

14. The composition of claim 13 wherein said fusion protein is encoded by an adenoviral expression vector encoding the TAA/ecdCD40L.

15. The composition of claim 13 wherein said fusion protein is encoded by a plasmid DNA expression vector encoding the TAA/ecdCD40L protein.

* * * * *

SEQUENCE LISTING

```
<160> NUMBER OF SEQ ID NOS: 1

<210> SEQ ID NO 1
<211> LENGTH: 279
<212> TYPE: PRT
<213> ORGANISM: Artificial Sequence
<220> FEATURE:
<223> OTHER INFORMATION: Synthetic Construct

<400> SEQUENCE: 1

Ala Glu Val Pro Gln Arg Leu Phe Pro Leu Arg Cys Leu Gln Ile Ser
1               5                   10                  15

Ser Phe Ala Asn Ser Ser Trp Thr Arg Thr Asp Gly Leu Ala Trp Leu
            20                  25                  30

Gly Glu Leu Gln Thr His Ser Trp Ser Asn Asp Ser Asp Thr Val Arg
        35                  40                  45

Ser Leu Lys Pro Trp Ser Gln Gly Thr Phe Ser Asp Gln Gln Trp Glu
    50                  55                  60

Thr Leu Gln His Ile Phe Arg Val Tyr Arg Ser Ser Phe Thr Arg Asp
65                  70                  75                  80

Val Lys Glu Phe Ala Lys Met Arg Leu Ser Tyr Pro Leu Ser Ala Gly
                85                  90                  95

Cys Glu Val His Pro Gly Asn Ala Ser Asn Asn Phe Phe His Val Ala
            100                 105                 110

Phe Gln Gly Lys Asp Ile Leu Ser Phe Gln Gly Thr Ser Trp Glu Pro
        115                 120                 125

Thr Gln Glu Ala Pro Leu Trp Val Asn Leu Ala Ile Gln Val Leu Asn
    130                 135                 140

Gln Asp Lys Trp Thr Arg Glu Thr Val Gln Trp Leu Leu Asn Gly Thr
145                 150                 155                 160

Cys Pro Gln Phe Val Ser Gly Leu Leu Glu Ser Gly Lys Ser Glu Leu
                165                 170                 175

Lys Lys Gln Val Lys Pro Lys Ala Trp Leu Ser Arg Gly Pro Ser Pro
            180                 185                 190

Gly Pro Gly Arg Leu Leu Leu Val Cys His Val Ser Gly Phe Tyr Pro
        195                 200                 205

Lys Pro Val Trp Val Lys Trp Met Arg Gly Glu Gln Glu Gln Gln Gly
    210                 215                 220

Thr Gln Pro Gly Asp Ile Leu Pro Asn Ala Asp Glu Thr Trp Tyr Arg
225                 230                 235                 240

Ala Thr Leu Asp Val Val Ala Gly Glu Ala Ala Gly Leu Ser Cys Arg
                245                 250                 255

Val Lys His Ser Ser Leu Glu Gly Gln Asp Ile Val Leu Tyr Trp Gly
            260                 265                 270

Gly Ser Tyr Thr Ser Ala Ala
        275
```